(12) United States Patent
Williams et al.

(10) Patent No.: US 11,001,554 B2
(45) Date of Patent: May 11, 2021

(54) LIPOPHILIC GUANIDINIUM COMPOUNDS FOR REMOVAL OF OXYANIONS FROM AQUEOUS SOLUTIONS

(71) Applicant: UT-Battelle, LLC, Oak Ridge, TN (US)

(72) Inventors: Neil J. Williams, Knoxville, TN (US); Radu Custelcean, Beavercreek, OH (US); Charles A. Seipp, Beavercreek, OH (US); Bruce A. Moyer, Oak Ridge, TN (US); Ross Ellis, Moss (NO); Carter W. Abney, Califon, NJ (US)

(73) Assignee: UT-Battelle, LLC, Oak Ridge, TN (US)

( * ) Notice: Subject to any disclaimer, the term of this patent is extended or adjusted under 35 U.S.C. 154(b) by 90 days.

(21) Appl. No.: 16/369,922

(22) Filed: Mar. 29, 2019

(65) Prior Publication Data
US 2019/0299124 A1 Oct. 3, 2019

Related U.S. Application Data

(60) Provisional application No. 62/649,801, filed on Mar. 29, 2018.

(51) Int. Cl.
*C07C 281/16* (2006.01)
*C02F 1/42* (2006.01)
(Continued)

(52) U.S. Cl.
CPC ........ *C07C 281/16* (2013.01); *B01D 11/0492* (2013.01); *B01J 41/07* (2017.01);
(Continued)

(58) Field of Classification Search
CPC .......................... C07C 281/16; C07C 281/18
(Continued)

(56) References Cited

U.S. PATENT DOCUMENTS 3,992,446 A * 11/1976 Tomcufcik ............ C07C 281/18
564/228
4,754,067 A * 6/1988 Addor .................... A01N 47/44
564/248

(Continued)

OTHER PUBLICATIONS

STIC composition search (Year: 2020).*
(Continued)

*Primary Examiner* — Clare M Perrin
(74) *Attorney, Agent, or Firm* — Scully, Scott, Murphy & Presser, P.C.

(57) ABSTRACT

Methods for removing an oxyanion from an aqueous source containing said oxyanion, comprising contacting said aqueous source with an aqueous-insoluble hydrophobic solution containing an oxyanion extractant compound dissolved in an aqueous-insoluble hydrophobic solvent to result in formation of an oxyanion salt of said extractant compound and extraction of said oxyanion salt into said aqueous-insoluble hydrophobic solution, wherein said extraction results in an extraction affinity (D) of said oxyanion of at least 1, wherein D is the concentration ratio of said oxyanion in the organic phase divided by the concentration of said oxyanion in the aqueous phase; wherein said extractant compound has the following composition:

(Continued)

wherein at least one of $R^1$-$R^{10}$ is or contains a hydrocarbon (R) group containing at least 4, 5, 6, 7, 8, 9, 10, 11, or 12 carbon atoms.

19 Claims, 3 Drawing Sheets

(51) Int. Cl.
  *B01J 41/09* (2017.01)
  *C02F 1/26* (2006.01)
  *B01J 41/07* (2017.01)
  *C07C 281/18* (2006.01)
  *B01D 11/04* (2006.01)
  *C22B 3/28* (2006.01)
  *B01J 41/04* (2017.01)
  *C07C 29/76* (2006.01)
  *C22B 3/26* (2006.01)

(52) U.S. Cl.
  CPC ............... *B01J 41/09* (2017.01); *C02F 1/26* (2013.01); *C02F 1/42* (2013.01); *C07C 281/18* (2013.01); *C22B 3/0013* (2013.01); *C22B 3/0016* (2013.01); *B01D 2257/70* (2013.01); *B01J 41/04* (2013.01); *C07C 29/76* (2013.01); *C22B 3/001* (2013.01); *C22B 3/0006* (2013.01)

(58) Field of Classification Search
  USPC .................................................. 564/227, 228
  See application file for complete search history.

(56) References Cited

U.S. PATENT DOCUMENTS

| | | | |
|---|---|---|---|
| 9,260,326 B2 | 2/2016 | Custelcean et al. | |
| 2013/0105745 A1* | 5/2013 | Xalter | C07C 279/02 252/601 |
| 2016/0075665 A1* | 3/2016 | Page | A61P 7/00 514/275 |
| 2016/0340299 A1* | 11/2016 | Peng | A61P 3/00 |
| 2017/0081223 A1 | 3/2017 | Hull et al. | |

OTHER PUBLICATIONS

Holger et al. (Supramolecular Chemistry, 1995, 5, 273-280). (Year: 1995).*

Custelcean R. et al., "Aqueous sulfate separation by crystallization of sulfate-water clusters", Angew. Chem. Int. Ed., 2015, 54, pp. 10525-10529.

Custelcean R. et al., "Aqueous sulfate separation by sequestration of [(SO4)2(H2O)4]4- clusters within highly insoluble imine-linked bis-guanidinium crystals", Chem. Eur. J., 2016, 22, pp. 1997-2003.

Salazar et al., "Equilibrium and Kinetic of Cr(VI) Extraction with Aliquat 336", Ind. Eng. Chem. Res. 1992, 31, pp. 1516-1522.

L. Karagiozov et al., "Separation of Molybdenum and Rhenium by Extraction With Mixtures of Trioctylamine and Aliquat 336 Followed by Selective Stripping", Hydrometallurgy, 4 (1979), pp. 51-55.

* cited by examiner

LIPOPHILIC GUANIDINIUM COMPOUNDS FOR REMOVAL OF OXYANIONS FROM AQUEOUS SOLUTIONS

CROSS REFERENCE TO RELATED APPLICATION

The present application claims benefit of U.S. Provisional Application No. 62/649,801, filed on Mar. 29, 2018, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to compositions useful for removing oxyanion species from aqueous solutions, such as removal of sulfate, phosphate, nitrate, chromate, selenate, arsenate, rhenate, or molybdate from water, and to methods for using such compositions in removing such species.

BACKGROUND OF THE INVENTION

Effective separation of highly hydrophilic anions (e.g., sulfate, phosphate, selenate, and chromate) from competitive aqueous solutions remains a major challenge, despite the tremendous progress in anion receptor chemistry over the past decade. In the particular case of sulfate, although a significant number of sulfate-binding receptors have been reported (e.g., I. Ravikumar et al, *Chem. Soc. Rev.,* 41, 3077, 2012), they have shown limited success in the substantial removal of this anion from water. A significant obstacle in the development of anion receptors is often the expensive multi-step synthesis required for their assembly, which generally involves tedious purifications and the use of toxic reagents and solvents.

The removal of superhydrophilic anions, such as sulfate and phosphate, from brines, agricultural runoff, and industrial waste continues to be an ongoing challenge. Seawater, in particular, contains very high levels of sulfate (~3,000 mg/L), and seawater is used on a large scale in oil-field injection operations. During such operations, the sulfate in the seawater combines with strontium and barium found in rock to form barium and strontium sulfate scale. The precipitation of barium and strontium sulfates is highly detrimental to the process, such as by clogging lines and destroying production wells. The conventional technology for removing sulfate from seawater is by nanofiltration, which can reduce sulfate levels to about 50 mg/mL. However, some drawbacks to this approach are the remaining high sulfate levels, the need to pressurize the system to 20-30 bars, which results in a significant expenditure in energy, and membrane fouling. Other methods involve scale-removing chemicals, but these are known to be difficult to use and very expensive, and they are not very effective against sulfate scales. Another technology, known as the MD-LPP process, yields sulfate-free seawater, but the process has the significant drawbacks of employing high pressures and pre-concentrating the seawater.

The difficulty in separating superhydrophilic anions, such as sulfate, from aqueous solutions can be attributed to their high free energies of hydration ($-1080$ kJ mol$^{-1}$ for sulfate) which makes their removal from aqueous solutions very unfavorable in comparison to less hydrophilic anions (e.g., $-381$ kJ mol$^{-1}$ for chloride) (e.g., Y. Marcus, *J. Chem. Soc. Faraday Trans.,* 1991, 87, 2995). Nevertheless, targeted separation of superhydrophilic anions from aqueous solutions is necessary for a range of important water treatment applications, including processing of radioactive wastes, oil production, and desalination. In a conventional method for separation of aqueous sulfate, the anion is hydrogen-bonded by cationic precipitants that are added to the aqueous phase (e.g., R. Custelcean et al., *Angew. Chem. Ed. Int.,* 54, 10525 (2015) and R. Custelcean et al., *Chem. Eur. J.,* 22, 1997 (2016)). This process is driven by the favorable lattice formation energy, which compensates for the unfavorable ion desolvation energy.

Liquid-liquid extraction is a common approach to ion separation, where ions are transported from water into an immiscible aliphatic solvent. However, liquid-liquid extraction has so far proven difficult for separation of superhydrophilic anions, such as sulfate, because (1) selectivity of anion extraction into oil generally follows the Hofmeister series, which favors extraction of less hydrophilic anions; and (2) hydrophilic ions and receptor groups are inherently unstable in aliphatic oil because of retention of their hydration shells, thereby causing uncontrolled aggregation and phase transitions. There would be a particular benefit in a liquid-liquid extraction process that could substantially remove superhydrophilic oxyanions, such as sulfate, from seawater or industrial waste by a straight-forward approach without the impediments and shortcomings of previous efforts.

SUMMARY OF THE INVENTION

The present disclosure describes a process for removing one or more types of oxyanions (e.g., sulfate, phosphate, or chromate) from an aqueous source by contacting the aqueous source with specialized lipophilic di-iminoguanidinium compounds that are particularly effective in extracting the oxyanion from aqueous solution into aqueous-insoluble hydrophobic solvents, thereby providing a highly efficient liquid-liquid extraction method for the removal of oxyanions, including superhydrophilic oxyanions. A notable feature of the lipophilic di-iminoguanidinium compounds described herein is the presence of one, two, three, four, or more hydrophobic (lipophilic) hydrocarbon groups containing at least or more than four, five, six, seven, or eight carbon atoms each. The lipophilic di-iminoguanidinium compounds described herein can advantageously extract one or more oxyanions, such as sulfate, nitrate, selenate, phosphate, arsenate, carbonate, bicarbonate, or metal oxyanion (e.g., chromate or rhenate) into an aqueous-insoluble non-polar solvent, in some cases selectively. The process described herein is advantageously straight-forward and cost-efficient while at the same time capable of removing a substantial portion or all of the oxyanion from an aqueous source.

The lipophilic di-iminoguanidinium compound (i.e., oxyanion extractant compound) has a structure within the following generic structure:

In Formula (I) above, $R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, (iii) —OR' groups, and (iv) —NR'$_2$ groups, wherein R' groups are independently selected from R groups and hydrogen atoms, provided that at least one of $R^1$, $R^2$, $R^3$, $R^4$, $R^5$, $R^6$, $R^7$, $R^8$, $R^9$, and $R^{10}$ is selected from: R groups containing 4-30 carbon atoms, or —OR groups with R containing 4-30 carbon atoms, or NR'$_2$ groups with at least one R' group being R containing 4-30 carbon atoms. The groups $R^{11}$ and $R^{12}$ are independently selected from hydrogen atom and methyl group. The species $X^{m-}$ is an anionic species with a magnitude of charge m, where in is an integer of at least 1; and n is an integer of at least 1, provided that n×m=1.

In particular embodiments, the method for removing one or more oxyanions from water involves contacting an oxyanion-containing aqueous source with an aqueous-insoluble hydrophobic solution containing an oxyanion extractant compound (i.e., the lipophilic di-iminoguanidinium compound) dissolved in an aqueous-insoluble hydrophobic solvent to result in formation of an oxyanion salt of the oxyanion extractant compound and extraction of the oxyanion salt into the aqueous-insoluble hydrophobic solution. In the method, $X^{m-}$ in Formula (1) is an anionic species exchangeable with the oxyanion in the aqueous source before the oxyanion extractant compound contacts the aqueous source, and $X^{m-}$ is the oxyanion in the oxyanion salt of the extractant compound. The extraction process generally results in an extraction affinity of the oxyanion (D) of at least 1, wherein D is the concentration ratio of the oxyanion in the organic phase divided by the concentration in the aqueous phase.

The invention provides receptor (extractant) compounds that include a family of compounds that can be tailored to treat industrial and agricultural aqueous solutions by removing high concentrations of oxyanions, such as sulfate, chromate, nitrate, phosphate, and the like, which are generally present in wastewater discharge from plants and factories, oil and gas production, or agricultural field run-off. Additionally, these compounds can be used to recover critical materials, such as rhenium, tellurium, and the like, which are often present in solutions in their oxyanion forms. The extractant compounds can also be used to regenerate scrubbing solutions used to remove $SO_x$ and $NO_x$ species from gaseous combustion processes. The extractant compounds are advantageously highly soluble in hydrocarbon-based solvents, such as kerosene or dodecane, which are often used in industrial solvent extractant processes. This permits a higher throughput of solutions that must be treated in a fast, efficient, and economical manner. Utilizing these compounds in a solvent extraction process allows for the repeated use of the compounds by continuously recycling of the solvent.

DETAILED DESCRIPTION OF THE INVENTION

As used herein, the term "hydrocarbon group" (also denoted by the group R) is defined as a chemical group composed solely of carbon and hydrogen, except that the hydrocarbon group may (i.e., optionally) be substituted with one or more fluorine atoms to result in partial or complete fluorination of the hydrocarbon group. In different embodiments, one or more of the hydrocarbon groups or linkers can contain precisely, or a minimum of, or a maximum of, for example, 1, 2, 3, 4, 5, 6, 7, 8, 9, 10, 12, 15, 18, 20, 22, 24, 26, 28, or 30 carbon atoms, or a number of carbon atoms within a particular range bounded by any two of the foregoing carbon numbers. Hydrocarbon groups in different compounds described herein, or in different positions of a compound, may possess the same or different number (or preferred range thereof) of carbon atoms in order to independently adjust or optimize such properties as the complexing ability, extracting (extraction affinity) ability, or selectivity of the compound.

In a first set of embodiments, the hydrocarbon group (R) is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-eicosyl, n-docosyl, n-tetracosyl, n-hexacosyl, n-octacosyl, and n-triacontyl groups.

In a second set of embodiments, the hydrocarbon group (R) is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 20 or 30 carbon atoms, wherein the "1-yl" suffix represents the point of attachment of the group.

In a third set of embodiments; the hydrocarbon group (R) is saturated and cyclic; i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In a fourth set of embodiments, the hydrocarbon group (R) is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2=CH-CH_2-$), 2-buten-1-yl ($CH_2-CH=CH-CH_2-$), butadienyl, 4-penten-1-yl, 3-penten-1-yl, 2-penten-1-yl, 5-hexen-1-yl, 4-hexen-1-yl, 3-hexen-1-yl, 3,5-hexadien-1-yl, 1,3,5-hexatrien-1-0, ethynyl; propargyl (2-propynyl); 3-butynyl, and the numerous other straight-chained alkenyl or alkenyl groups having up to 20 or 30 carbon atoms.

In a fifth set of embodiments, the hydrocarbon group (R) is unsaturated and branched, i.e., a branched olefinic or alkenyl group. Some examples of branched olefinic groups include propen-2-yl 1-buten-2-yl 1-buten-3-yl ($CH_2=CH-CH.-CH_3$), 1-propen-2-methyl-3-yl ($CH_2=C(CH_3)-CH_2-$), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 20 or 30 carbon atoms, wherein the dot in any of the foregoing groups indicates a point of attachment.

In a sixth set of embodiments, the hydrocarbon group (R) is unsaturated and cyclic, i.e., a cycloalkenyl group. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl; cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems.

In one aspect, the invention is directed to specialized lipophilic compounds (i.e., oxyanion extractant compounds, or "extractant compounds") that have an ability to complex with an oxyanion and transfer (extract) the oxyanion from an aqueous solution into an aqueous-insoluble non-polar solution in which the oxyanion extractant compound is dissolved. The extractant compound contains a di-iminoguanidinium moiety and at least two phenyl rings, at least one of which is functionalized with a hydrocarbon group containing at least or more than four, five, six, seven, or eight carbon atoms.

The extractant di-iminoguanidinium) compound has a structure within the scope of the following generic structure:

(1)

In Formula (I) above, $R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, as described above, (iii) —OR' groups, and (iv) —NR'$_2$ groups, wherein R' groups are independently selected from R groups and hydrogen atom. In the case where at least one of $R^1$-$R^{10}$ is an —OR' group with R' being H, the —OR' group is an —OH (hydroxy) group. In the case where at least one of $R^1$-$R^{10}$ is an —NR'$_2$ group with at least one R' being H, the —NR'$_2$ group may be an —NHR or —NH$_2$ group. The groups $R^{11}$ and $R^{12}$ are independently selected from hydrogen atom and methyl group. Thus, in different embodiments, both $R^{11}$ and $R^{12}$ are hydrogen atoms; or only one of $R^{11}$ and $R^{12}$ is a hydrogen atom with the other being methyl; or both $R^{11}$ and $R^{12}$ are methyl groups. In the case of an —OR group, the —OR group may alternatively be attached to the phenyl ring in Formula (1) via a one-, two-, or three-carbon linker, such as a —CH$_2$—OR, —CH$_2$CH$_2$—OR, or —CH$_2$CH$_2$CH$_2$—OR group. Moreover, in some embodiments, R groups present in any two adjacent $R^1$-$R^{10}$ groups can interconnect, thus creating a bicyclic ring system, such as naphthyl, in the structure shown in Formula (1).

In Formula (1), $X^{m-}$ is an anionic species with a magnitude of charge m, where m is an integer of at least 1, provided that n×m=1. The variable n is any number that, when multiplied with m, results in 1. Thus, where the anionic species is a halide (−1 charge, e.g., chloride), n and m are both 1. However, where the anionic species is sulfate (−2 charge), n is ½ and m is 2, which indicates more than one extractant compound associated with each sulfate.

In embodiments where $R^{11}$ and $R^{12}$ are both hydrogen atoms, Formula (1) reduces to the following sub-formula:

(1a)

For purposes of the invention, at least one (i.e., one or more) of $R^1$, $R^2$, $R^3$, $R^4$, $R^5$, $R^6$, $R^7$, $R^8$, $R^9$, and $R^{10}$ is or includes a lipophilic R group containing at least or more than 4 carbon atoms, such as any of the hydrocarbon (R) groups described above (e.g., alkyl or alkenyl) having at least 4 carbon atoms. In some embodiments, the one or more lipophilic R groups contain at least or more than 5, 6, 7, 8, 9, 10, 11, or 12 carbon atoms and up to, for example, 15, 20, 25, or 30 carbon atoms. In a first set of embodiments, at least (or more than) one, two, three, or four of $R^1$-$R^{10}$ are hydrocarbon (R) groups containing at least 4, 5, 6, 7, 8, 9, 10, 11, or 12 and up to 15, 18, 20, 22, 24, 26, 28, or 30 carbon atoms, or a carbon number within a range bounded by any two of the foregoing values (e.g., 4-30, 5-30, 6-30, 7-30, 8-30, 9-30, 10-30, 11-30, 12-30, 4-20, 6-20, 8-20, 12-20, 4-15, 4-12, 6-15, or 6-12 carbon atoms). In a second set of embodiments, at least (or more than) one, two, three, or four of $R^1$-$R^{10}$ are —OR groups in which the hydrocarbon (R) group contains at least 4, 5, 7, 8, 9, 10, 11, or 12 and up to 15, 18, 20, 22, 24, 26, 28, or 30 carbon atoms, or a carbon number within a range bounded by any two of the foregoing values (e.g., 4-30, 5-30, 6-30, 7-30, 8-30, 9-30, 10-30, 11-30, 12-30, 4-20, 6-20, 8-20, 12-20, 4-15, 4-12, 6-15, or 6-12 carbon atoms). In a third set of embodiments, at least (or more than) one, two, three, or four of $R^1$-$R^{10}$ are —$NR'_2$ groups in which one or both R' groups are hydrocarbon (R) groups containing at least 4, 5, 6, 7, 8, 9, 10, 11, or 12 and up to 15, 18, 20, 22, 24, 26, 28, or 30 carbon atoms, or a carbon number within a range bounded by any two of the foregoing values (e.g., 4-30, 5-30, 6-30, 7-30, 8-30, 9-30, 10-30, 11-30, 12-30, 4-20, 6-20, 8-20, 12-20, 4-15, 4-12, 6-15, or 6-12 carbon atoms).

In a first particular set of embodiments, at least two, three, four, five, or six of $R^1$, $R^2$, $R^3$, $R^4$, $R^5$, $R^6$, $R^7$, $R^8$, $R^9$, and $R^{10}$ (or more typically, at least two, three, four, five, or six of $R^2$, $R^3$, $R^4$, $R^7$, $R^8$, and $R^9$) are independently selected from: R groups containing 4-30 carbon atoms, or —OR groups with R containing 4-30 carbon atoms, or —$NR'_2$ groups with at least one R' group being lit containing 4-30 carbon atoms.

In a second particular set of embodiments, at least two, three, four, five, or six of $R^1$, $R^2$, $R^3$, $R^4$, $R^5$, $R^6$, $R^7$, $R^8$, $R^9$, and $R^{10}$ (or more typically, at least two, three, four, five, or six of $R^2$, $R^3$, $R^4$, $R^7$, $R^8$, and $R^9$) are independently selected from: R groups containing 5-30 carbon atoms, or —OR groups with R containing 5-30 carbon atoms, or —$NR'_2$ groups with at least one R' group being lit containing 5-30 carbon atoms.

In a third particular set of embodiments, at least two, three, four, five, or six of $R^1$, $R^2$, $R^3$, $R^4$, $R^5$, $R^6$, $R^7$, $R^8$, $R^9$, and $R^{10}$ (or more typically, at least two, three, four, five, or six of $R^2$, $R^3$, $R^4$, $R^7$, $R^8$, and $R^9$) are independently selected from: R groups containing 6-30 carbon atoms, or —OR groups with R containing 6-30 carbon atoms, or —$NR'_2$ groups with at least one R' group being R containing 6-30 carbon atoms.

In a fourth particular set of embodiments, at least two, three, four, five, or six of $R^1$, $R^2$, $R^3$, $R^4$, $R^5$, $R^6$, $R^7$, $R^8$, $R^9$, and $R^{10}$ (or more typically, at least two, three, four, five, or six of $R^2$, $R^3$, $R^4$, $R^7$, $R^8$, and $R^9$) are independently selected from: R groups containing 7-30 carbon atoms, or —OR groups with R containing 7-30 carbon atoms, or —$NR'_2$ groups with at least one R' group being R containing 7-30 carbon atoms.

In a fifth particular set of embodiments, at least two, three, four, five, or six of $R^1$, $R^2$, $R^3$, $R^4$, $R^5$, $R^6$, $R^7$, $R^8$, $R^9$, and $R^{10}$ (or more typically, at least two, three, four, five, or six of $R^2$, $R^3$, $R^4$, $R^7$, $R^8$, and $R^9$) are independently selected from: R groups containing 8-30 carbon atoms, or —OR groups with R containing 8-30 carbon atoms, or —$NR'_2$ groups with at least one R' group being R containing 8-30 carbon atoms.

In a sixth particular set of embodiments, (i) precisely or at least one, two, or three of $R^1$, $R^2$, $R^3$, $R^4$, and $R^5$ (or more typically, precisely or at least one, two, or three of $R^2$, $R^3$ and $R^4$) are independently selected from: R groups containing 4-30 carbon atoms, or —OR groups with R containing 4-30 carbon atoms, or $NR'_2$ groups with at least one R' group being R containing 4-30 carbon atoms, and/or (ii) precisely or at least one, two, or three of $R^6$, $R^7$, $R^8$, $R^9$, and $R^{10}$ (or more typically, at least one, two, or three of $R^7$, $R^8$, and $R^9$) are independently selected from: R groups containing 4-30 carbon atoms, or —OR groups with R containing 4-30 carbon atoms, or NR', groups with at least one R' group being R containing 4-30 carbon atoms.

In a seventh particular set of embodiments, (i) precisely or at least one, two, or three of $R^1$, $R^2$, $R^3$, $R^4$, and (or more typically, at least one, two, or three of $R^2$, $R^3$, and $R^4$) are independently selected from: R groups containing 5-30 carbon atoms, or —OR groups with R containing 5-30 carbon atoms, or NR', groups with at least one R' group being R containing 5-30 carbon atoms, and/or (ii) precisely or at least one, two, or three of $R^6$, $R^7$, $R^8$, $R^9$, and $R^{10}$ (or more typically, at least one, two, or three of $R^7$, $R^8$, and $R^9$) are independently selected from: R groups containing 5-30 carbon atoms, or —OR groups with R containing 5-30 carbon atoms, or $NR'^2$ groups with at least one R' group being R containing 5-30 carbon atoms.

In an eighth particular set of embodiments, (i) precisely or at least one, two, or three of $R^1$, $R^2$, $R^3$, $R^4$, and $R^5$ (or more typically, at least one, two, or three of $R^2$, $R^3$, and $R^4$) are independently selected from: R groups containing 6-30 carbon atoms, or —OR groups with R containing 6-30 carbon atoms, or $NR'_2$ groups with at least one R' group being R containing 6-30 carbon atoms, and/or (ii) precisely or at least one, two, or three of $R^6$, $R^7$, $R^8$, $R^9$, and $R^{10}$ (or more typically, at least one, two, or three of $R^7$, $R^8$, and $R^9$) are independently selected from: R groups containing 6-30 carbon atoms, or —OR groups with R containing 6-30 carbon atoms, or NR', groups with at least one R' group being R containing 6-30 carbon atoms.

In a ninth particular set of embodiments, (i) precisely or at least one, two, or three of $R^1$, $R^2$, $R^3$, $R^4$ and $R^5$ (or more typically, at least one, two, or three of $R^2$, $R^3$, and $R^4$) are independently selected from: R groups containing 7-30 carbon atoms, or —OR groups with R containing 7-30 carbon atoms, or $NR'_2$ groups with at least one R' group being R containing 7-30 carbon atoms, and/or (ii) precisely or at least one, two, or three of $R^6$, $R^7$, $R^8$, $R^9$, and $R^{10}$ (or more typically, at least one, two, or three of $R^7$, $R^8$, and $R^9$) are independently selected from: R groups containing 7-30 carbon atoms, or —OR groups with R containing 7-30 carbon atoms, or $NR'_2$ groups with at least one R' group being R containing 7-30 carbon atoms.

In an tenth particular set of embodiments, (i) precisely or at least one, two, or three of $R^1$, $R^2$, $R^3$, $R^4$, and $R^5$ (or more typically, at least one, two, or three of $R^2$, $R^3$, and $R^4$) are independently selected from: R groups containing 8-30 carbon atoms, or —OR groups with R containing 8-30 carbon atoms, or NR', groups with at least one R' group being R containing 8-30 carbon atoms, and/or (ii) precisely or at least one, two, or three of $R^6$, $R^7$, $R^8$, $R^9$, and $R^{10}$ (or more typically, at least one, two, or three of $R^7$, $R^8$, and $R^9$) are independently selected from: R groups containing 8-30 carbon atoms, or —OR groups with R containing 8-30 carbon atoms, or $NR'_2$ groups with at least one R' group being R containing 8-30 carbon atoms.

Moreover, although Formula (1) depicts a specific tautomeric arrangement, Formula (1) is intended to include any other tautomers that can be derived from or interconvert with the tautomer shown in Formula (1). As well known, tautomeric structures have the same atomic connections (aside from one or more protons) but differ in the placement of double bonds, generally with concomitant relocation of one or more protons.

The anionic species ($X^{m-}$) may be any anionic species that, when complexed as a salt with the di-aminoguanidinium portion shown in Formula (1), can be exchanged for another anionic species desired to be removed from an aqueous solution. As the different anionic species have different dissociation constants, any anionic species may be useful in exchanging with another anionic species to be removed from an aqueous source. The anionic species may also represent a species that has been removed from an aqueous solution, wherein the resulting salt of the extracted anion and di-aminoguanidinium portion shown in Formula (1) is valuable as a precursor for producing a neutral form of Formula (1) or for recovering a metal present in the oxyanion (e.g., rhenium), or the salt can be used as an extractant compound that can exchange with another anionic species. The anionic species ($X^{m-}$) can be, for example, a halide, such as fluoride, chloride, bromide, or iodide. The anionic species can alternatively be a halide equivalent (or pseudohalide), such as methanesulfonate (mesylate), trifluoromethanesulfonate (triflate), tosylate, cyanate, thiocyanate, cyanide, or a sulfonamide anion, such as bis(trifluoromethane) sulfonamide (i.e., bistriflimide). The anionic species may alternatively be a borate anion, such as tetrafluoroborate, tetrakis(pentafluorophenyl)borate, or tetrakis[3,5-bis(trifluoromethyl)phenyl]borate. The anionic species may alternatively be hexafluorophosphate ($PF_6^-$). The anionic species may alternatively be hydroxide, or an alkoxide (e.g., methoxide or ethoxide). The anionic species may alternatively be a carboxylate species, such as formate, acetate, propionate, or glycolate. In other embodiments, the anionic species ($X^{m-}$) can be an oxyanion, typically included in the structure by extraction from an aqueous solution.

As used herein, the term "oxyanion" refers to an anion having at least three or four oxygen atoms, wherein the oxygen atoms are generally all bound to a central element. Some examples of oxyanions include sulfate (e.g., $SO_4^{2-}$), nitrate ($NO_3^-$), chromate (e.g., $CrO_4^{2-}$), selenite (e.g. $SeO_3^{2-}$), selenate (e.g., $SeO_4^{2-}$), tellurate (e.g., $TeO_4^{2-}$, $TeO_6^{6-}$, or $H_5TeO_6^-$), arsenite ($AsO_3^{3-}$ or $AsO_2^-$), phosphate (e.g., $PO_4^{3-}$), arsenate ($AsO_4^{3-}$), carbonate ($CO_3^{2-}$), bicarbonate ($HCO_3^-$), and perchlorate ($ClO_4^-$). Some of the oxyanions, such as chromate, are metal oxyanions. Other metal oxyanions include, for example, rhenate, tungstate, vanadate, molybdate, and stannate. The metal in the metal oxyanion is typically a transition metal (e.g., any of Groups 3-12 of the Periodic Table) or a main group metal (e.g., Groups 13, 14, 15, or 16 of the Periodic Table). The oxyanions provided above may or may not also include related derivatives. For example, unless otherwise stated, the term "sulfate" may also include thiosulfate ($S_2O_3^{2-}$), bisulfate ($HSO_4^-$), and sulfite ($SO_3^{2-}$). Similarly, the term "chromate" may also include $Cr_2O_7^{2-}$ (dichromate). Similarly, the term "phosphate" may also include hydrogenphosphate ($HPO_4^{2-}$), dihydrogenphosphate ($H_2PO_4^-$), pyrophosphate ($P_2O_7^{4-}$), thiosphosphates (e.g., $PO_3S^{3-}$ or $PO_2S_2^{3-}$), and phosphite (e.g., $PO_3^{3-}$, $HPO_3^{2-}$, or $H_2PO_3^-$).

The compounds according to Formula (1) can be synthesized by methods well known in the art. For example, to produce compounds according to Formula (1) in which at least one of $R^1$-$R^{10}$ is an —OR group, with R containing at least four carbon atoms, a hydroxy-containing benzaldehyde (e.g., 3,4-dihydroxybenzaldehyde) can be reacted with an iodine salt of R (i.e., $R^+I^-$) under conditions conducive to Williamson ether synthesis to produce the respective ether-containing benzaldehyde, and the ether-containing benzaldehyde reacted with 1,3-diaminoguanidinium chloride to afford a di(imino)guanidinium compound according to Formula (1). Similarly, to produce compounds according to Formula (1) in which at least one of $R^1$-$R^{10}$ is an —NHR or —$NR_2$ group, with R containing at least four carbon atoms, an amine-containing benzaldehyde (e.g., 4-aminobenzaldehyde) can be reacted with an iodine salt of R (i.e., $R^+I^-$) to alkylate the amine and produce the respective alkylated aminobenzaldehyde, and the alkylated aminobenzaldehyde reacted with 1,3-diaminoguanidinium chloride to afford a di(imino)guanidinium compound according to Formula (1). In the case where at least one of $R^1$-$R^{10}$ is an R group directly attached to a benzene ring in Formula (1), the compound can be synthesized by, for example, reacting an alkyl-substituted benzaldehyde (e.g., 4-butylbenzaldehyde, 4-hexylbenzaldehyde, or 4-octylbenzaldehyde) with 1,3-diaminoguanidinium chloride to afford the di(imino)guanidinium compound according to Formula (1). An exemplary synthetic scheme is provided in the Examples section below.

In another aspect, the invention is directed to a method for removing one or more oxyanions from an aqueous source containing the oxyanion by contacting the aqueous source with any of the lipophilic di-iminoguanidinium extractant compounds described above, wherein the anionic species ($X^{m-}$) in Formula (1), before contact with the aqueous source, is exchangeable with the oxyanion to be removed from the aqueous source. In some embodiments, the anionic species in Formula (1), before contact with the aqueous source, is more specifically a halide, pseudohalide, or nitrate. The oxyanion(s) in the aqueous source can be one or more of any of the oxyanions described above. The aqueous source can be any source (e.g., industrial waste or discharge, agricultural run-off, or seawater) containing one or more oxyanions to be removed. The oxyanion to be removed is generally present in the aqueous source as an inorganic salt that is dissolved or suspended in the aqueous source. In some cases, at least one of the oxyanions is in the form of an insoluble scale, such as $CaSO_4$, $SrSO_4$, or $BaSO_4$ scale. Scale is often a major problem in oil field injection operations and the method described herein offers a solution to scale removal. The oxyanion may also be a metal oxyanion, as often found in effluent from a metal processing or metal mining operation. The aqueous medium is typically composed predominantly or completely of water, such as found in seawater, water from sewage treatment, or aqueous effluent from an industrial or commercial process. However, in some embodiments, the aqueous medium may include an organic solvent miscible in water, such as an alcohol, acetone, or the like.

The anionic species ($X^{m-}$) in the di-iminoguanidinium compound of Formula (1), before being contacted with and dissolved into the aqueous source, should be capable of being replaced with the oxyanion to be removed from the aqueous source. For example, the di-iminoguanidinium compound of Formula (1) may take the anionic species ($X^{m-}$) as a halide, pseudohalide, or nitrate before contact of the di-iminoguanidinium compound of Formula (1) with the aqueous source, in a situation where the oxyanion to be removed from the aqueous source is sulfate, nitrate, selenite, selenate, phosphite, phosphate, arsenite, arsenate, carbonate, bicarbonate, perchlorate, or metal oxyanion.

In the method, the extractant compound according to Formula (1) is first dissolved in an aqueous-insoluble hydrophobic solvent. The aqueous-insoluble hydrophobic solvent can be any of the hydrophobic organic solvents known in the art that are substantially or completely immiscible with water or aqueous solutions in general. The aqueous-insoluble hydrophobic solvent is typically a hydrocarbon solvent, which may be non-halogenated (e.g., hexanes, heptanes, octanes, decanes, dodecanes, benzene, toluene, xylenes, kerosene, or petroleum ether), or halogenated (e.g., methylene chloride, chloroform, carbon tetrachloride, 1,2-dichlorethane, trichloroethylene, and perchloroethylene), or etherified (e.g., diethyl ether or diisopropyl ether), or combination of halogenated and etherified (e.g., bis(chloroethyl) ether and 2-chloroethyl vinyl ether). The aqueous source containing the oxyanion (to be extracted) is then contacted with the aqueous-insoluble hydrophobic solution containing the extractant compound dissolved in the aqueous-insoluble hydrophobic solvent to result in formation of an oxyanion salt of the extractant compound and extraction of the oxyanion salt of the extractant compound into the aqueous-insoluble hydrophobic solution (organic phase). The term "contacted" or "contacting," as used herein in reference to contacting of the aqueous and organic phases, generally refers to an intimate mixing of the aqueous and organic phases so as to maximize extraction of the oxyanion from the aqueous phase to the organic phase. Methods of intimately mixing liquids are well known in the art. For example, the aqueous and organic phases may be placed in a container and the container agitated. Following contact, the two phases are generally separated by means well known in the art. The foregoing described process amounts to an efficient liquid-liquid extraction process whereby one or more oxyanions in an aqueous solution is/are extracted, in some cases selectively, into the aqueous-insoluble hydrophobic solvent (organic phase). The extraction process is generally capable of achieving an extraction affinity (D) of the oxyanion of at least 1, wherein D is the concentration ratio of the oxyanion in the organic phase divided by its concentration in the aqueous phase. In some embodiments, a D value of greater than 1 is achieved, such as a. D value of at least or above 2, 5, 10, 20, 50, 100, 150, 200, 250, 500, or 1000. The selectivity of the process can be characterized by the separation factor (SF), wherein SF is calculated as the ratio of D for two different ions, such as any two of the ions described above, such as selectivity of sulfate over chloride, in which particular case $SF=D_{sulfate}/D_{chloride}$. Selectivity is generally evident in an SF value greater than 1. In some embodiments, an SF value of at least or greater than 2, 5, 10, 20, 50, 100, 150, 200, 250, 500, or 1000 is achieved.

In the process described above for removing one or more oxyanions from an aqueous source, the resulting extracted salt can be conveniently processed to regenerate the starting extractant compound according to Formula (1). By regenerating the starting extractant compound, the process can advantageously include a recycling step, which makes the process further cost effective with minimal environmental impact. To regenerate the starting extractant compound, the extracted salt (e.g., Formula (1) in which $X^{m-}$ is sulfate) can be reacted with a base (e.g., a metal hydroxide, organic amine, or ammonia) that converts the cationic form of the extractant compound, according to Formula (1), to a neutral form while at the same time forming a byproduct salt (e.g., metal sulfate, organoammonium sulfate, or ammonium sulfate, respectively) with the oxyanion. The neutral version of the compounds in Formula (1) can then reacted with a protic acid (e.g., HCl, HBr, or $HNO_3$, etc.) to produce the original cationic form according to Formula (1) with $X^{m-}$ being the conjugate base of the acid used (e.g., $Cl^-$, $Br^-$, or $NO_3^-$, respectively).

Examples have been set forth below for the purpose of illustration and to describe certain specific embodiments of the invention. However, the scope of this invention is not to be in any way limited by the examples set forth herein.

EXAMPLES

Synthesis of a Di(Imnoguanidinium) (DIG) Compound

A di(imino)guanidinium (DIG) extractant compound having lipophilic functionalities on both sides of a hydrophilic (guanidinium) anion-binding core was prepared. The multiple branched aliphatic chains in this design optimizes the hydrophilic-lipophilic balance (HLB), which was found to impart exceptional solubility in aliphatic oils.

The synthetic process used in preparing the DIG compounds is summarized by the following scheme:

The synthesis of the DIG anion receptor is shown in Scheme 1. DIG was made by a simple three-step synthesis with a high overall synthetic yield of 68.8%, a marked improvement compared with other lipophilic guanidinium receptors (typically <10-15%). In brief, the three steps consisted of the following reactions: an Appel reaction converting commercially available branched aliphatic alcohol to the corresponding aliphatic halide (wherein step "a" includes imidazole, iodine, and triphenylphosphine), a Williamson ether synthesis to attach the lipophilic-chains to the benzaldehyde (wherein step "b" includes 3,4-dihydroxybenzaldehyde and potassium carbonate), and an imine condensation reaction with diaminoguanidinium chloride to form the final DIG (wherein step "c" includes 1,3-diaminoguanidinium chloride).

Sulfate extraction by the chloride form of cationic receptors can be represented as the molecular mechanism according to Formula (2), wherein "org" and "L" denote the organic-phase species and the extractant respectively (B. A. Moyer et al, *Inorg. Chem.*, 52, 3473, 2013).

$$2[L^+.Cl^-]_{org}+SO_4^{2-}(aq) \rightleftharpoons [L^+_2.SO_4^{2-}]_{org}+2Cl^-(aq) \qquad (2)$$

However, complex mechanisms are more frequently encountered where molecular aggregates are involved with various stoichiometry (x, y) according to Formula (3) (R. Custelcean et al., *Chem. Eur. J.*, 22, 1997, 2016):

$$\frac{y}{x}[L_x^+Cl_x^-]_{org} + SO_4^{2-}(aq) \rightleftharpoons [L_y^+Cl_{(y-2)}^-SO_4^{2-}]_{org} + 2Cl^-(aq) \quad (3)$$

The extraction equilibrium and the performance of the extractant is often characterized by conducting liquid-liquid extraction experiments with varying extractant concentrations and monitoring the distribution of the target ion (sulfate, as $^{35}SO_4^{2-}$) between the phases. The extraction affinity of the system is quantified by the parameter D, the concentration ratio of ion in the organic phase divided by the concentration in the aqueous phase. The selectivity of the system is characterized by the separation factor (SF), which is the ratio of D for two different ions. For example, the preference of a receptor for sulfate over chloride is calculated as SF=$D_{SO4}/D_{Cl}$. Typically, high values for D and SF are desired for extraction processes. Values for D and SF for DIG were compared with the industrial anion exchange reagent Aliquat® 336 (A336), which is a commercially available alkylated quaternary ammonium chloride used for a range of anion separation purposes (P. A. Tasker et al., *Comprehensive Coordination Chemistry II*, Elsevier Ltd, New York, 9, 759, 2004). However, the limited solubility of A336-sulfate in hydrocarbon solvents necessitates comparative studies to be performed using the halogenated hydrocarbon solvent 1,2-dichloroethane (1,2-DCE). As DIG was found to be highly soluble in paraffinic hydrocarbon solvents, additional experiments using an application-relevant liquid-liquid extraction solvent (Isopar L, isoparaffin C-12 average) were conducted. To reflect conditions usually encountered in sulfate separation applications, the study was conducted using a 100-fold excess of chloride vs. sulfate in the aqueous phase.

Figure 1A:
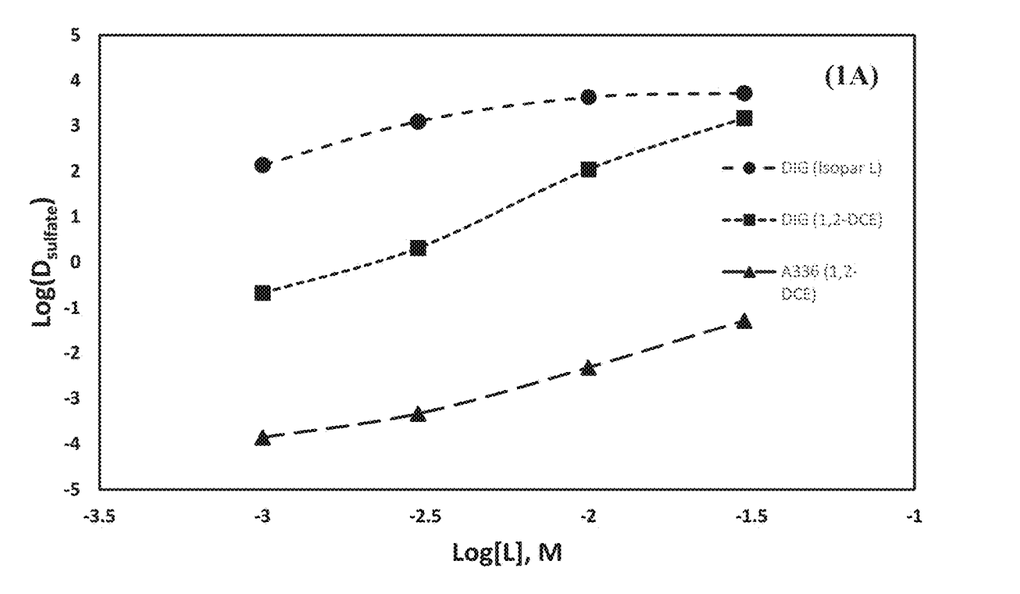
FIG. 1A is a plot of Log(D) for sulfate plotted against the Log[L], where (D) is the sulfate distribution ratio (i.e., extraction affinity of the extractant for sulfate) and [L] is the concentration of extractant. The aqueous phase was 0.1 mmol $Na_2SO_4$ and 10 mmol NaCl. The solutions were mixed at 25.0±0.2° C.
Figure 1B:
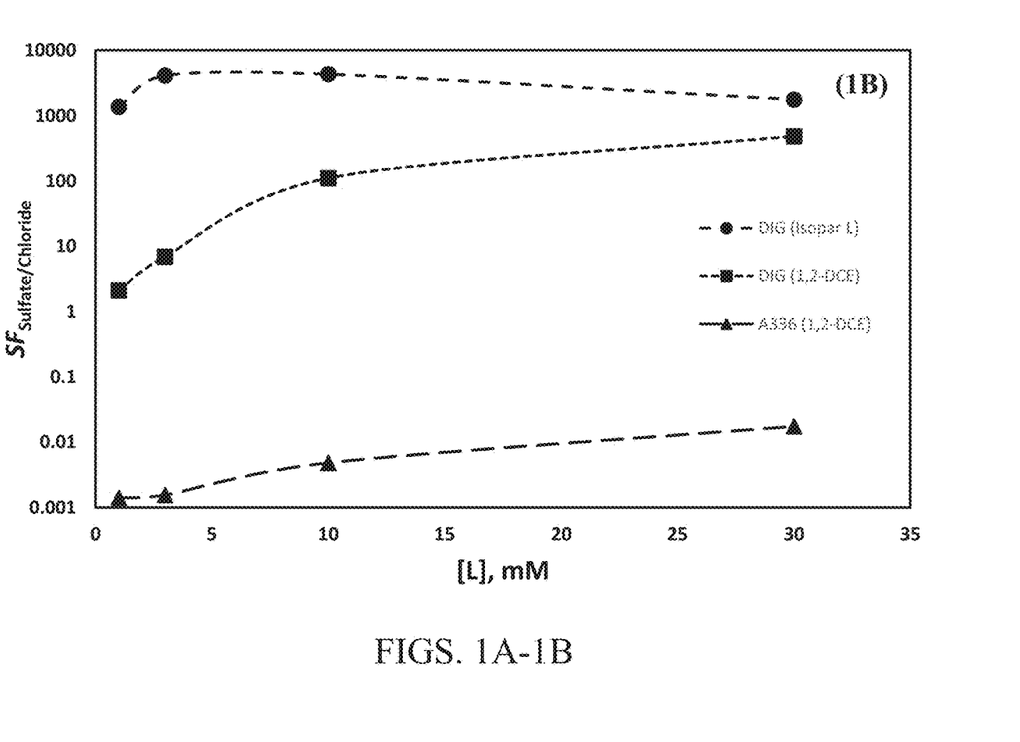
FIG. 1B is a plot comparing separation factors (SF) for sulfate over chloride for various concentrations of DIG and Aliquat® 336 (a commercial quaternary ammonium salt). SF is defined here as the ratio $D_{sulfate}/D_{chloride}$.

FIGS. 1A and 1B show extraction data for log(D) vs. log[L] and [L] vs. SF, respectively, for DIG and A336. Across the concentration range, the I) values for A336 are below 0.06, with a maximum SF of 0.02. These low values show that, as expected, A336 is not effective for liquid-liquid separation of sulfate from chloride. In comparison, DIG reaches a maximum D of >4,000 and SF of >4,000. These very high values for D and SF are unprecedented for liquid-liquid extraction of superhydrophilic anions, where achievements of SF>1 (sulfate vs. chloride) are rare. The gradients of the slopes for log(D) versus log[L] are related to the stoichiometry of the extractant-ion species before and after extraction. For example, a gradient of 2 is consistent with the mechanism outlined in equilibrium (1). If aggregates are involved, as shown in equilibrium (2), then the gradient will be y/x. The extraction experiments for DIG and A336 in 1,2-DCE show gradients that are close to 2, suggesting that extraction is approximately consistent with equilibrium (1). However, extraction for DIG in the aliphatic hydrocarbon (Isopar L) has a non-linear dependence, with an apparent change in slope from ~2 at low concentration to ~0.3 at higher concentration. This suggests that the extraction mechanism is concentration-dependent, perhaps with the formation of aggregates.

Figure 2A:
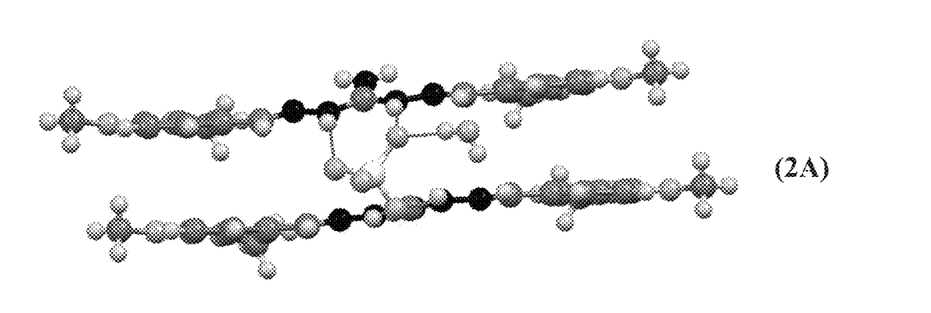
FIG. 2A is a crystal structure of two modified DIG receptors binding to a partially hydrated sulfate along the edge and axis of the sulfate.
Figure 2B:
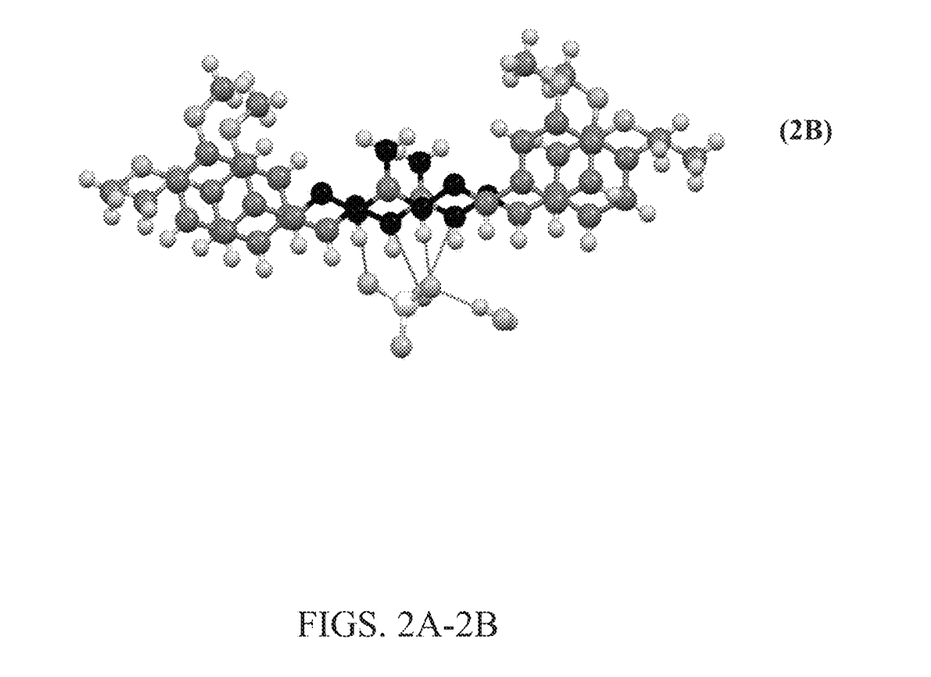
FIG. 2B depicts a network of DIGS surrounding the sulfate.

As discussed above, the success of the recently reported iminoguanidinium crystallizing agents was attributed to the binding of partially-hydrated anions, circumventing unfavorable desolvation energy (R. Custelcean et al., *Angew. Chem. Ed. Int.*, 54, 10525, 2015; R. Custelcean et al., *Chem. Eur. J.*, 22, 1997, 2016). The crystal structure of the modified DIG-sulfate complex is shown in FIG. 2A. As further shown in FIG. 2B, the complex contains a partially-hydrated sulfate with a network of DIG receptors complexed to the partially hydrated sulfate.

To investigate the role of water in the formation of stable receptor-anion complexes in the oil phase, the uptake of water by DIG-chloride in oil was measured. These measurements revealed that there was an increase in the concentration of water in the oil phase, after mixing with water. The amount of water present in the oil phase increased from an average of a half a water to two waters per a DIG after mixing with water. This increase suggests that water is involved in the solvation of both the DIG-chloride and most likely the DIG-sulfate species in the oil phase.

Figure 3A:
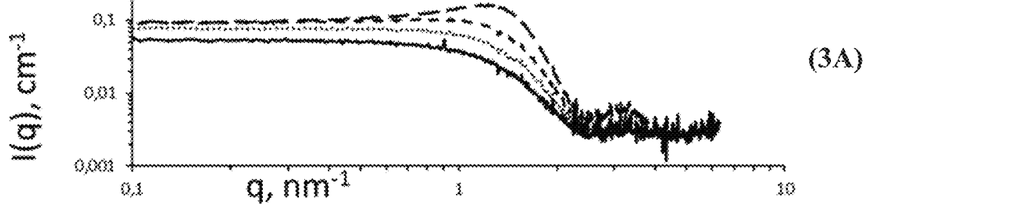
FIG. 3A is a small-angle X-ray scattering (SAXS) analysis for varying DIG-chloride concentration in Isopar L (extraction solvent) after mixing with water.

The presence of appreciable concentrations of water in oil, as well as the formation of aggregates (as suggested by the extraction data in FIGS. 1A and 1B), suggests that reverse micelles may be present. Reverse micelles form in amphiphile-oil-water mixtures to minimize exposure of the hydrophilic solutes to the hydrophobic solvent, and manifest as nanoscale polar clusters made up from water, ions, and amphiphile 'head-groups'. To investigate the structure of the proposed reverse micelles, small-angle X-ray scattering (SAXS) measurements were performed with varying concentration of DIG in Isopar L. SAXS works on the principle that X-rays interact with fluctuations in electron density within a material and are scattered, thus yielding information on nanoscale morphology. For reverse micelles, the electron-dense cores scatter X-rays against the surrounding aliphatic medium. FIG. 3A shows the SAXS data after subtracting the incoherent scattering from the background Isopar L solvent. The form of the scattering data are typical for "particle scattering," which is consistent with reverse micellar aggregates. With increasing extractant concentration, a broad correlation peak emerges at q=1.5 nm$^{-1}$, which is typical for concentrated colloidal systems that do not flocculate (i.e., particles that repel) (J. Eastoe et al., *Adv. Colloid Interface Sci.*, 36, 1, 1991). This suggests that DIG forms nanoscale colloidal structures in Isopar L that remain particle-like in nature across a large concentration range, without flocculation or growth into interconnected mesophases.

Figure 3B:
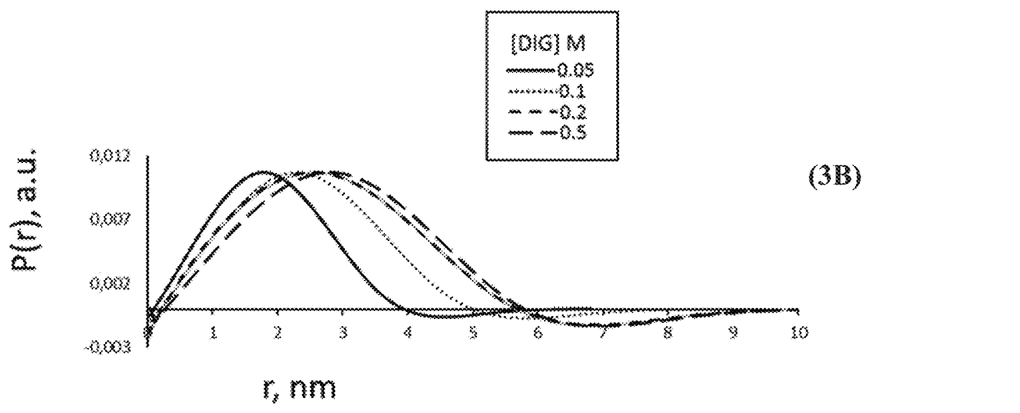
FIG. 3B is the corresponding pair distance (P(r)) distribution function (PDDF) analysis.
Figure 3C:
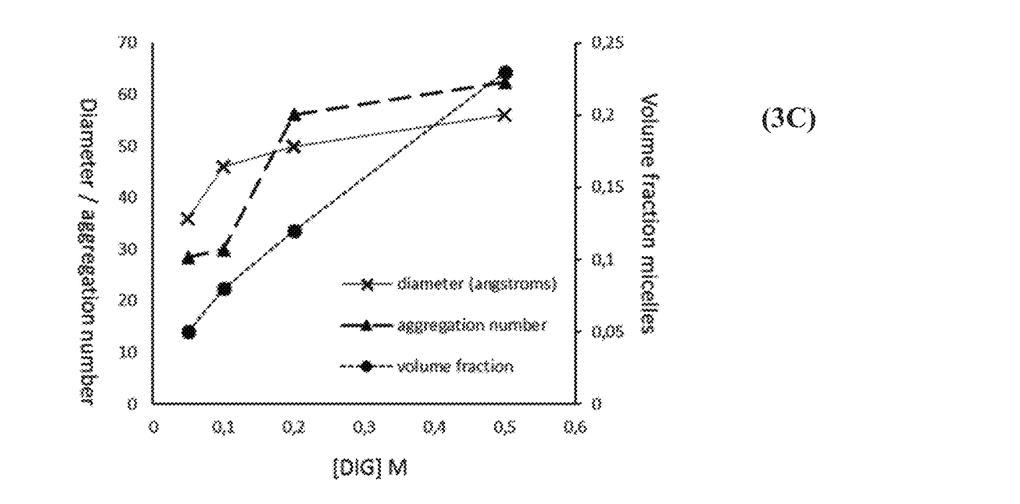
FIG. 3C is a plot of the variation of micelle volume fraction (bottom line), diameter (angstrom), and DIG aggregation (number) with concentration.

To derive real-space information from the scattering data, the generalized indirect Fourier transform (GIFT) method was applied using the Percus-Yevick hardsphere structure factor model to account for the interactions at concentrated conditions (this method is described in numerous publications, such as G. Fritz et al., *J. Phys.: Condens. Matter*, 18, S2403, 2006 & G. Fritz et al., *J. Chem. Phys.*, 113, 9733, 2000). The GIFT analysis generates pair distance distribution functions (PDDFs, as shown in FIG. 3B) from the scattering data that correspond to the average morphology of the scattering particles. Across the concentration range, the PDDFs are all bell-shaped functions that are consistent with spherical particles (O. Glatter, *J. Appl. Crystallogr.*, 12, 166, 1979). The volume fraction of these particles (assumed to be inverted micelles), their average radius and aggregation number of DIG per scattering particle (calculated from the GIFT analysis) is presented in FIG. 3C. This shows that increasing DIG concentration drives the formation of colloidal particles that increase moderately in volume fraction, size, and aggregation number. An increase in aggregation number of DIG-chloride species is consistent with a decrease in the slope of the extraction data in FIG. 1A. The metrics presented in FIG. 3C are comparable to the large reverse micelles encountered in water-in-oil microemulsions stabilized by surfactants (J. Eastcoe et al., supra), which suggests that DIG behaves like a surfactant in the liquid-liquid system. These large reverse micelles are remarkably stable to flocculation and mesophase formation across the concentration range, especially considering the water-saturating conditions.

The above described DIG receptor is remarkable in both the unparalleled high selectivity for sulfate over chloride as well as the unique ability to solubilize the superhydrophilic ion pairs in the aliphatic hydrocarbon solvent. Previous crystallization studies suggest that the remarkable ability of iminoguanidinium groups to separate sulfate originates from the binding of the partially hydrated anion (R. Custelcean, 2015 and 2016, supra). This previous work, as well as the high water concentration in the oil that coincides with the formation of reverse micelles, indicates that sulfate-water clusters are also extracted by the DIG receptor used in the liquid-liquid system described above. Sulfate is known to require 12 H-bond donors to satisfy its coordination sphere (e.g., B. P. I-lay et al., J. Am. Chem. Soc., 127, 1810, 2005), and these cannot come from the aliphatic Isopar L solvent (unlike DCE), It is difficult to envision a structure that would allow several DIG receptors to saturate the sulfate coordination sphere in a manner that is consistent with the extraction data. Therefore, the data suggests that the significant quantities of water in the oil, likely in reverse micelles, is involved in solvating the extracted superhydrophilic anion. The remarkable propensity to form spherical colloid-like aggregates that resist flocculation across a wide concentration range allows this reagent to be deployed at high concentrations, as needed for many process applications.

In summary, a new anion receptor is herein reported that provides unparalleled selectivity for sulfate over chloride in a liquid-liquid extraction system. The remarkable selectivity and stable phase properties may originate from the extraction of partially hydrated anions into reverse micelles. In addition to a six orders-of-magnitude increase in sulfate vs. chloride selectivity (relative to an industrial benchmark), the exemplified receptor is relatively simple, easily synthesized, and is uniquely compatible with application-relevant solvents. The above exemplified extractant is advantageously selective and process-compatible for sulfate. The above described process finally provides a highly effective liquid-liquid separation process for superhydrophilic anions.

While there have been shown and described what are at present considered the preferred embodiments of the invention, those skilled in the art may make various changes and modifications which remain within the scope of the invention defined by the appended claims.

What is claimed is:

1. A compound having the following structure:

(1)

wherein:
$R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, (iii) —OR' groups, and (iv) —NR'$_2$ groups, wherein R' groups are independently selected from R groups and hydrogen atoms, provided that at least four of $R^1$, $R^2$, $R^3$, $R^4$, $R^5$, $R^6$, $R^7$, $R^8$, $R^9$, and $R^{10}$ are selected from: R groups containing 4-30 carbon atoms, or —OR groups with R containing 4-30 carbon atoms, or —NR'$_2$ groups with at least one R' group being R containing 4-30 carbon atoms;

$R^{11}$ and $R^{12}$ are independently selected from hydrogen atom and methyl group;

$X^{m-}$ is an anionic species with a magnitude of charge m, where m is an integer of at least 1; and n is a number, provided that n×m=1.

2. The compound of claim 1, provided that at least four of $R^1$, $R^2$, $R^3$, $R^4$, $R^5$, $R^6$, $R^7$, $R^8$, $R^9$, and $R^{10}$ are selected from: R groups containing 6-30 carbon atoms, or —OR groups with R containing 6-30 carbon atoms, or —NR'$_2$ groups with at least one R' group being R containing 6-30 carbon atoms.

3. The compound of claim 1, provided that:
(i) at least two of $R^1$, $R^2$, $R^3$, $R^4$, and $R^5$ are selected from: R groups containing 4-30 carbon atoms, or —OR groups with R containing 4-30 carbon atoms, or —NR'$_2$ groups with at least one R' group being R containing 4-30 carbon atoms, and
(ii) at least two of $R^6$, $R^7$, $R^8$, $R^9$, and $R^{10}$ are selected from: R groups containing 4-30 carbon atoms, or —OR groups with R containing 4-30 carbon atoms, or —NR'$_2$ groups with at least one R' group being R containing 4-30 carbon atoms.

4. The compound of claim 1, provided that:
(i) at least two of $R^1$, $R^2$, $R^3$, $R^4$, and $R^5$ are selected from: R groups containing 6-30 carbon atoms, or —OR groups with R containing 6-30 carbon atoms, or —NR'$_2$ groups with at least one R' group being R containing 6-30 carbon atoms, and
(ii) at least two of $R^6$, $R^7$, $R^8$, $R^9$, and $R^{10}$ are selected from: R groups containing 6-30 carbon atoms, or —OR groups with R containing 6-30 carbon atoms, or —NR'$_2$ groups with at least one R' group being R containing 6-30 carbon atoms.

5. The compound of claim 1, wherein $X^{m-}$ is halide or nitrate.

6. The compound of claim 1, wherein $X^{m-}$ is sulfate or phosphate.

7. A method for removing an oxyanion from an aqueous source containing said oxyanion, the method comprising contacting said aqueous source with an aqueous-insoluble hydrophobic solution containing an oxyanion extractant compound dissolved in an aqueous-insoluble hydrophobic solvent to result in formation of an oxyanion salt of said oxyanion extractant compound and extraction of said oxyanion salt of said oxyanion extractant compound into said aqueous-insoluble hydrophobic solution, wherein said extraction results in an extraction affinity (D) of said oxyanion of at least 1, wherein D is the concentration ratio of said oxyanion in the organic phase divided by the concentration of said oxyanion in the aqueous phase;

wherein said oxyanion extractant compound has the following structure:

(1)

wherein:

$R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, (iii) —OR' groups, and (iv) —NR'$_2$ groups, wherein R' groups are independently selected from R groups and hydrogen atoms, provided that at least one of $R^1$, $R^2$, $R^3$, $R^4$, $R^5$, $R^6$, $R^7$, $R^8$, $R^9$, and $R^{10}$ is selected from: R groups containing 4-30 carbon atoms, or —OR groups with R containing 4-30 carbon atoms, or —NR'$_2$ groups with at least one R' group being R containing 4-30 carbon atoms;

$R^{11}$ and $R^{12}$ are independently selected from hydrogen atom and methyl group;

$X^{m-}$ is an anionic species with a magnitude of charge m, where m is an integer of at least 1, provided that $X^{m-}$ is an anionic species exchangeable with the oxyanion in said aqueous source before said oxyanion extractant compound contacts said aqueous source, and $X^{m-}$ is said oxyanion in the oxyanion salt of said oxyanion extractant compound; and n is a number, provided that n×m=1.

8. The method of claim 7, wherein said oxyanion is selected from the group consisting of sulfate, nitrate, selenate, tellurate, phosphate, arsenate, carbonate, bicarbonate, perchlorate, and metal oxyanions.

9. The method of claim 7, wherein said oxyanion is sulfate or phosphate.

10. The method of claim 7, wherein $X^{m-}$ is halide or nitrate before said oxyanion extractant compound contacts said aqueous source.

11. The method of claim 7, provided that at least two of $R^1$, $R^2$, $R^3$, $R^4$, $R^5$, $R^6$, $R^7$, $R^8$, $R^9$, and $R^{10}$ are independently selected from: R groups containing 4-30 carbon atoms, or —OR groups with R containing 4-30 carbon atoms, or —NR'$_2$ groups with at least one R' group being R containing 4-30 carbon atoms.

12. The method of claim 7, provided that at least four of $R^1$, $R^2$, $R^3$, $R^4$, $R^5$, $R^6$, $R^7$, $R^8$, $R^9$, and $R^{10}$ are independently selected from: R groups containing 4-30 carbon atoms, or —OR groups with R containing 4-30 carbon atoms, or —NR'$_2$ groups with at least one R' group being R containing 4-30 carbon atoms.

13. The method of claim 7, provided that at least one of $R^1$, $R^2$, $R^3$, $R^4$, $R^5$, $R^6$, $R^7$, $R^8$, $R^9$, and $R^{10}$ is selected from: R groups containing 6-30 carbon atoms, or —OR groups with R containing 6-30 carbon atoms, or —NR'$_2$ groups with at least one R' group being R containing 6-30 carbon atoms.

14. The method of claim 7, provided that at least two of $R^1$, $R^2$, $R^3$, $R^4$, $R^5$, $R^6$, $R^7$, $R^8$, $R^9$, and $R^{10}$ are independently selected from: R groups containing 6-30 carbon atoms, or —OR groups with R containing 6-30 carbon atoms, or —NR'$_2$ groups with at least one R' group being R containing 6-30 carbon atoms.

15. The method of claim 7, provided that at least four of $R^1$, $R^2$, $R^3$, $R^4$, $R^5$, $R^6$, $R^7$, $R^8$, $R^9$, and $R^{10}$ are independently selected from: R groups containing 6-30 carbon atoms, or —OR groups with R containing 6-30 carbon atoms, or —NR'$_2$ groups with at least one R' group being R containing 6-30 carbon atoms.

16. The method of claim 7, provided that:

(i) at least one of $R^1$, $R^2$, $R^3$, $R^4$, and $R^5$ is selected from: R groups containing 4-30 carbon atoms, or —OR groups with R containing 4-30 carbon atoms, or —NR'$_2$ groups with at least one R' group being R containing 4-30 carbon atoms, and (ii) at least one of $R^6$, $R^7$, $R^8$, $R^9$, and $R^{10}$ is selected from: R groups containing 4-30 carbon atoms, or —OR groups with R containing 4-30 carbon atoms, or —NR'$_2$ groups with at least one R' group being R containing 4-30 carbon atoms.

17. The method of claim 7, provided that:

(i) at least two of $R^1$, $R^2$, $R^3$, $R^4$, and $R^5$ are selected from: R groups containing 4-30 carbon atoms, or —OR groups with R containing 4-30 carbon atoms, or —NR'$_2$ groups with at least one R' group being R containing 4-30 carbon atoms, and (ii) at least two of $R^6$, $R^7$, $R^8$, $R^9$, and $R^{10}$ are selected from: R groups containing 4-30 carbon atoms, or —OR groups with R containing 4-30 carbon atoms, or —NR'$_2$ groups with at least one R' group being R containing 4-30 carbon atoms.

18. The method of claim 7, provided that:

(i) at least one of $R^1$, $R^2$, $R^3$, $R^4$, and $R^5$ is selected from: R groups containing 6-30 carbon atoms, or —OR groups with R containing 6-30 carbon atoms, or —NR'$_2$ groups with at least one R' group being R containing 6-30 carbon atoms, and (ii) at least one of $R^6$, $R^7$, $R^8$, $R^9$, and $R^{10}$ is selected from: R groups containing 6-30 carbon atoms, or —OR groups with R containing 6-30 carbon atoms, or —NR'$_2$ groups with at least one R' group being R containing 6-30 carbon atoms.

19. The method of claim 7, provided that:

(i) at least two of $R^1$, $R^2$, $R^3$, $R^4$, and $R^5$ are selected from: R groups containing 6-30 carbon atoms, or —OR groups with R containing 6-30 carbon atoms, or —NR'$_2$ groups with at least one R' group being R containing 6-30 carbon atoms, and (ii) at least two of $R^6$, $R^7$, $R^8$, $R^9$, and $R^{10}$ are selected from: R groups containing 6-30 carbon atoms, or —OR groups with R containing 6-30 carbon atoms, or —NR'$_2$ groups with at least one R' group being R containing 6-30 carbon atoms.

* * * * *